United States Patent [19]

Kawasaki et al.

[11] Patent Number: 5,066,462

[45] Date of Patent: Nov. 19, 1991

[54] ANALYTICAL ELEMENT FOR MEASURING ENZYME ACTIVITY

[75] Inventors: Kazuya Kawasaki; Mitsutoshi Tanaka; Yoshikazu Amano; Harumi Katsuyama, all of Saitama, Japan

[73] Assignee: Fuji Photo Film Co., Ltd., Kanagawa, Japan

[21] Appl. No.: 401,494

[22] Filed: Aug. 29, 1989

Related U.S. Application Data

[63] Continuation of Ser. No. 126,770, Nov. 30, 1987, abandoned.

[30] Foreign Application Priority Data

Nov. 28, 1986 [JP] Japan .................. 61-283628

[51] Int. Cl.$^5$ .................. G01N 21/01; C12Q 1/48
[52] U.S. Cl. .................. 422/56; 422/57; 435/15; 435/805; 436/170

[56] References Cited

U.S. PATENT DOCUMENTS

| | | | |
|---|---|---|---|
| 3,183,173 | 5/1965 | William | 422/56 |
| 4,246,342 | 1/1981 | Misaki et al. | 435/810 |
| 4,258,001 | 3/1981 | Pierce et al. | 435/805 |
| 4,450,232 | 5/1984 | Sanford et al. | 422/57 |
| 4,547,465 | 10/1985 | Eikenberry | 422/56 |

*Primary Examiner*—Robert J. Warden
*Assistant Examiner*—Lyle Alfandary Alexander
*Attorney, Agent, or Firm*—McAulay Fisher Nissen Goldberg & Kiel

[57] ABSTRACT

A dry-type analytical element suitable for measuring the activity of alanine aminotransferase in a liquid sample, characterized by incorporating a dye capable of absorbing the electromagnetic waves of 400 to 500 nm into at least one water-permeable layer. The coloring sensitivity of the dry-type analytical element does not increase substantially even under a fluorescent light, and thereby, an accurate measured value can easily be obtained.

15 Claims, No Drawings

ANALYTICAL ELEMENT FOR MEASURING ENZYME ACTIVITY

This is a continuation of application Ser. No. 07/126,770, filed Nov. 30, 1987, now abandoned.

BACKGROUND OF THE INVENTION

1. Field of the Invention

This invention relates to a dry-type analytical element for measuring enzyme activity, and particularly, suitable for measuring the activity of alanine aminotransferase in a liquid sample.

2. Description of the Prior Art

A dry-type analytical element suitable for measuring alanine aminotransferase (ALT) activity in a liquid sample is known. Such an element has at least one water-permeable layer containing α-ketoglutaric acid and alanine or salt(s) thereof, and the pyruvic acid produced is detected. In such analytical elements, coloring sensitivity sometimes increases during the handling required for measurement, and as a result, the previously prepared calibration curve cannot be utilized.

SUMMARY OF THE INVENTION

The present inventors have investigated this problem, and have found that the coloring sensitivity increases when the AST activity assay element is left under a light, particularly under a fluorescent light.

An object of the invention is to provide a dry-type analytical element suitable for measuring the ALT activity in a liquid sample in which increase of the coloring sensitivity during handling is prevented, and thereby, an accurate measured value can easily be obtained.

Such an object can be achieved by incorporating a dye capable of absorbing the electromagnetic waves of 400 to 500 nm into at least one water-permeable layer of the dry type analytical element.

Thus, the present invention provides a dry-type analytical element suitable for measuring the activity of alanine aminotransferase in a liquid sample. The element has one or more water-permeable layers wherein, at least one of the water-permeable layers is a porous spreading layer, at least one of the water-permeable layers contains alanine or its salt and α-ketoglutaric acid or its salt, and at least one of the water-permeable layers contains a dye capable of absorbing the electromagnetic radiation having the wave length in range of 400 to 500 nm.

DETAILED DESCRIPTION OF THE INVENTION

The dye to be utilized in the analytical element of the invention is the dye capable of absorbing the electromagnetic radiation having the wave length in the range of 400 to 500 nm. Preferably, the dye has a maximum absorption in the above wave length range. Water-soluble aqueous medium can also be utilized. The dye utilizable in the invention are cyanine dyes, merocyanine dyes, styryl dyes, oxonol dyes, hemioxonol dyes and acidic azo dyes and the like. The oxonol dyes, hemioxonol dyes and acidic azo dyes having pyrazolone ring are preferable because the effect of the invention remarkably appears Such dyes include the monomethine oxonol dyes and hemioxonol dyes having a pyrazolone ring of which the 1-position is substituted by a phenyl group having at least one sulfo group and the 3-position is substituted by an alkyl group, carboxyl group, an alkoxycarbonyl group, hydroxyl group, an alkoxyl group or the like, the acidic azo dyes having a pyrazolone ring of which 1-position is substituted by a phenyl group having at least one sulfo group and 3-position is substituted by an alkyl group, carboxyl group, an alkoxycarbonyl group or the like, and the acidic azo dyes having a pyrazolone ring of which 1 position is substituted by phenyl group, 3-position is substituted by an alkyl group, carboxyl group, an alkoxycarbonyl group or the like, and 4-position is substituted by a phenylazo group having at least one sulfo group. Para-position of the benzene ring of the hemioxonol dyes is usually substituted by a dialkylamino group or an alkoxyl group. The para-position may be substituted by a water soluble group such as the sulfo group. Examples of the dye suitable for the analytical element of the invention include 4,4'-monomethine-bis-(1-(p-sulfophenyl)-3 methyl-5-pyrazolone1oxonol, 1-(p-sulfophenyl)-3-methyl-4-(p-dimethylaminobenzylidene)pyrazolone, C. I. Acid Yellow 11, C. I. Acid Yellow 17, C. I. Acid Yellow 23 (Tartrazine), C. 1. Acid Yellow 25, C. I. Acid Yellow 29, C. I. Acid Yellow 40, C. I. Acid Yellow 42 and C. I. Acid Yellow 76. The minimum content of the dye is the amount necessary to prevent the increase of coloring sensitivity, and usually it is 30 μmole preferably 50 μmole per 1 $m^2$ of analytical element. On the other hand, the maximum amount is determined by the background color concentration produced by the dye itself, that is, the absorbance in the absorption region of the color indicator employed for the assay. For example, in the case of Tartrazine, it is about 0.4 m mol. per 1 $m^2$ of analytical element.

In a dry-type analytical element for measuring ALT activity, alanine and α-ketoglutaric acid are usually employed as a substrate to produce pyruvic acid, and hydrogen peroxide is generated from the pyruvic acid in the presence of pyruvate oxidase. The hydrogen peroxide reacts with an indicator usually in the presence of peroxidase to form a color, and this color is measured. Suitable contents of alanine and α-ketoglutaric acid are 0.5 to 10 m mol./$m^2$, and preferable contents are 1 to 5 m mol./$m^2$.

These substrates, reactive components and enzymes may be incorporated in a porous spreading layer or other water permeable layers. However, alanine and ° ketoglutaric acid or their salts are preferably incorporated in the porous spreading layer, and peroxidase and the indicator are preferably incorporated in another layer. Alanine, α-ketoglutaric acid or their salts may also be incorporated in a layer other than the porous spreading layer, such as, a reagent layer or binding layer.

The indicator may be selected from described in Japanese Patent KOKAI 49-53888, 51-40191, 53-131089 and 55-124499. The leuco pigments described in U.S. Pat. No. 4,089,747, Japanese Patent KOKAI 59-193352 and Japanese Patent Application No. 59-124412 are also usable. Furthermore, Trinder reagent cited in Japanese Patent KOKOKU 58-28277 and the indicator composition described in Japanese Patent KOKAI 59-54962 are also usable.

Peroxidase usable in the analytical element is, for example, described in Japanese Patent KOKAI 50-137192.

Pyruvate oxidase (POP) may be any enzyme capable of catalyzing the reaction to produce acetyl phosphate, carbon dioxide and hydrogen peroxide from pyruvate, inorganic phosphate and oxygen, but POP produced by culturing a microorganism belonging to genus *Pediococcus*, *Streptococcus* or *Aerococcus* are preferable. Suitable POP are, for example, described in Japanese patent KOKAI 55-13068 and 59-162877. The suitable content of POP is $3 \times 10^3$ to $10^5$ IU/m$^2$, and a preferable content is $5 \times 10^3$ to $5 \times 10^4$ IU/m$^2$.

Phosphate source may be phosphate ion $PO_4^{3-}$, hydrogenphosphate ion $HPO_4^{2-}$ or dihydrogenphosphate ion $H_2PO_4$ in a form of acid or salt. It also may be phosphate ester or phosphate complex capable of producing any of the above ions by hydrolysis. A phosphate buffer solution is also usable as the phosphate source Such a phosphate source may be incorporated in the porous spreading layer or another layer. The content of the phosphate source is usually 0.1 micromol to 10 micromol per 1 IU of POP.

Coenzymes, such as, thiamine pyrophosphate (TPP) and flavin adenine dinucleotide (FAD) are preferably allowed to coexist with POP. As TPP, thiamine diphosphate is preferable, and its content is usually 5 nmol. to 500 nmol., preferably 10 nmol. to 300 nmol. per 1 U of POP.

Divalent or trivalent metal ions, such as, $Ca^{2+}$, $Mg^{2+}$, $Co^{2+}$, $Mn^{2+}$ and $Al^{3+}$ are also preferably allowed to coexist with POP. These are added in a form of salt, such as, manganese chloride, manganese phosphate, manganese hydrogenphosphate, magnesium chloride and magnesium hydrogenphosphate. The content of the metal ion is usually 5 nmol. to 200 μmol. preferably 10 nmol. to 100 μmol. per 1 U of POP.

A suitable pH for pyruvate oxidase is in the range of 6.5 to 8.0, and the water-permeable layer containing pyruvate oxidase may contain a pH buffer capable of adjusting the pH of this layer to the above range. Examples of such a pH buffer includes the compositions corresponding to a phosphate buffer solution, a tris-HCl buffer solution and a Good's buffer solution as is disclosed in Biochemistry, Vol. 5, No. 2, pp 467 to 477 (1966).

The porous spreading layer may contain a hydrophilic polymer, such as, polyvinyl pyrrolidone and polyacrylamide or a surfactant, such as, nonionic surfactants including polyoxyethylene nonionic surfactants, anionic surfactants including alkylsulfonate surfactants and cationic surfactants including quaternary ammonium salt surfactants.

Other water-permeable layers may also contain the above hydrophilic polymer or the surfactant.

The present invention can be applied to various known dry type analytical elements The analytical element may be multilayer element containing a support, a registration layer, a light blocking layer, a reagent layer, a porous spreading layer, an adhesive layer, a filtering layer, a water-absorption layer, an undercoating layer and other known layers. Some embodiments are disclosed in U.S. Pat. No. 3,992,158, 4,042,335 and Japanese Patent KOKAI 5-164356.

The following embodiments are practically employable as the analytical elements of the invention containing a support:

(1) A spreading layer also utilized as a reagent layer superposed on the support. A water-absorption layer may be incorporated between the spreading layer and the support.

(2) A spreading layer, a reagent layer and the support superposed in this order. A water absorption layer may be incorporated between the reagent layer and the support. The Yellow dye of the invention is incorporated in either or both of the spreading layer and the reagent layer.

(3) A spreading layer, a reagent layer, a registration layer and the support superposed in this order. The yellow dye is incorporated in either or both of the spreading layer and the reagent layer.

(4) A spreading layer, a light-reflecting layer, a reagent layer and the support superposed in this layer. One or more of spreading layer, light-reflecting layer and the reagent layer contain the yellow dye.

(5) A spreading layer also utilized as a reagent layer, a light-reflecting layer, a registration layer and the support superposed in this order. The spreading layer contains the yellow dye.

(6) A spreading layer, a light-reflecting layer, a reagent layer, a registration layer and the support superposed in this order. At least, one of the spreading layer, the light-blocking layer and the reagent layer contains the yellow dye.

(7) A spreading layer, a reagent layer, a light-reflecting layer, a registration layer and the support superposed in this order. At least, the spreading layer or the reagent layer contains the yellow dye.

(8) A spreading layer, a first reagent layer, a light-reflecting layer, a second reagent layer, a registration layer and the support superposed in this order. At least, the second reagent layer or one of the layers located on the side contrary to the support therefrom contains the yellow dye.

Preferable embodiments for the present invention are (2) and (4). In any embodiment of (2) to (8), a water absorption layer may be incorporated between the reagent layer or the registration layer and the support. In the embodiment of (2) or (3), a filtering layer may be incorporated between the reagent layer and the registration layer or the spreading layer or between plural reagent layers. In any embodiment of (4) to (8), a filtering layer may be incorporated between the light-reflecting layer and the spreading layer, the reagent layer or the registration layer, between the reagent layer and the registration layer, between the spreading layer and the reagent layer, or between the first reagent layer and the second reagent layer.

In the dry-type analytical element of the invention, a substrate may be incorporated in two or more layers, such as, a spreading layer and a reagent layer, a reagent layer and a light-reflecting layer, a first reagent layer and a second reagent layer or a spreading layer and a first reagent layer, or one of the above combinations and other layer(s). In this case, the contents of the substrate may be different from each other. Pyruvate oxidase may also be incorporated in two or more layers, such as, a spreading layer and a reagent layer, a reagent layer and a light reflecting layer, and the contents of the enzyme may be different from each other.

The water-impermeable light-transmissive support includes a transparent film made of polyethylene terephthalate, polycarbonate, polystyrene, cellulose ester such as cellulose triacetate and cellulose acetate propionate, or the like. The thickness of the support is usually in the range of about 50 μmm to about 1 mm, preferably from about 80 μmm to about 300 μmm. The support may be provided with an under coating layer on its surface in order to strengthen the adhesion of the layer laminated on it, such as, a registration layer. Instead of the undercoating layer, the surface of the support may be treated by a physical activation, such as, glow discharge or corona discharge or by a chemical activation.

The registration layer or the water-absorption layer provided on the support is preferably composed of a hydrophilic binder, that is a hydrophilic polymer which absorbs water to swell. The registration layer is the layer where a color material produced from the indicator diffuses, and the water-absorption layer is the layer where the color material cannot substantially diffuse. The hydrophilic polymer is generally a natural or synthetic hydrophilic polymer having a swelling ratio in the range of about 1.5 to about 20, preferably from about 2.5 to about 15 at a water absorption at 30° C. Examples of the hydrophilic polymer are gelatins, such as, alkali-treated gelatin, acid-treated gelatin and deionized gelatin, gelatin derivatives, such as, phthalated gelatin, agarose, polyacrylamide, polyvinyl alcohol and polyvinyl pyrrolidone. The thickness of the registration layer and water-absorption layer are usually in the range of about 1 μm to about 50 μmm preferably about 3 μmm to 30 μm in the dry state. These layers may contain a surfactant, such as, a cationic surfactant, an anionic surfactant, an ampholytic surfactant or a nonionic surfactant and a pH buffer.

A binding layer may be provided for laminating a spreading layer on a water absorption layer, registration layer, light-reflecting layer, filtering layer, reagent layer or the like. The binding layer is preferably composed of a hydrophilic polymer capable of adhering to the spreading layer when the binding layer is dampened or absorbs water to swell. Such a hydrophilic polymer may be selected from the hydrophilic polymers usable for the registration layer described above. Preferable hydrophilic polymers are gelatins, gelatin derivatives, polyacrylamide and the like. The thickness of the binding layer is usually in the range of about 0.5 μm to about 20 μm, preferably about 1 μm to about 10 μm in dry state. The binding layer may be provided for the binding of other layers. The binding layer is formed by applying an aqueous solution of a hydrophilic polymer and other compounds may be added, if necessary.

The reagent layer of the analytical element of the invention may contain a hydrophilic polymer and a pH buffer, if necessary. Examples of the hydrophilic polymer include starch, cellulose, agarose, gelatin and their derivatives, cellulose derivatives, such as, hydroxyethyl cellulose and hydroxypropyl methyl cellulose, polyacrylamide, copolymers of acrylamide and various vinyl monomer, polymethacrylamide, copolymers of methacrylamide and various vinyl monomers, polyvinyl alcohol, polyvinyl pyrrolidone, and copolymers of vinylpyrrolidone and various vinyl monomers. Preferable hydrophilic polymers are polyvinyl alcohol, polyvinyl pyrrolidone, polyacrylamide polymethacrylamide and cellulose derivatives. pH buffers suitable for the reagent layer include carbonate buffers, borate buffers, phosphate buffers and Good's buffers. Examples of these buffers are described in "Tanpakushitsu.Koso no Kiso-Jikken Ho (Fundamental Experimental Method of Proteins, Enzymes)" (Horio et al., Nankodo, Japan, 1981).

The light-reflecting layer blocks the color of the sample spotted on the spreading layer, preventing the light of the color from penetrating into reagent layer and transparent support. In the case of a whole blood sample, the color is due to hemoglobin. The light blocking effect takes place at the time of measuring the optically detectable change, such as, the color change or coloration occurring in the registration layer, reagent layer or other layer(s) from the side of the light-transmissive support by reflection photometry. This layer not only functions as a light-blocking layer but also as a background layer. The light-reflecting layer is preferably a water-permeable layer composed of a hydrophilic polymer as a binder wherein light-reflecting particles a such as a titanium dioxide or barium sulfate are dispersed. Examples of the hydrophilic polymer having film-forming property include the foregoing hydrophilic polymers usable for the registration layer, weakly hydrophilic regenerated cellulose and cellulose acetate. Preferable hydrophilic polymers are gelatins, gelatin derivatives and polyacrylamide. A known hardening agent may be added to the gelatin or a gelatin derivative. The light-reflecting layer may be formed by applying an aqueous solution of a hydrophilic polymer wherein titanium dioxide particles or the like are suspended followed by drying. In the analytical element of the invention, titanium dioxide particles or the like may be incorporated in other layer(s), such as, the spreading layer, reagent layer or registration layer.

The spreading layer preferably has a metering action. The metering action is such that a sample spotted on the spreading layer spreads at a fixed amount per unit area without uneven distribution of any component in the sample in horizontal directions. The material constituting the matrix of the spreading layer may be filter paper, nonwoven fabric, woven fabrics, such as, plain weaves, knitted fabrics, such as, tricot fabric, glass fiber filter paper, membrane filter formed of blushed polymer, and three-dimensional lattice structure material composed of polymer particulates, etc. Preferable materials for the spreading layer are fibrous materials, such as, woven fabrics and knitted fabrics. These are explained in detail in U.S. Pat. No. 4,292,272, GB 2,087,074A and EP 0,162,302A. These woven fabrics and knitted fabrics are preferably degreased, such as, by washing.

The dry-type analytical element of the invention is preferably cut into square or circular pieces having a side or diameter of about 15 mm to about 30 mm, and put in a slide frame disclosed in Japanese Patent KOKAI 57-63452, U.S. Pat. No. 4,169,751, 4,387,990, PCT application WO 83/00391, etc. to use.

The measurement is carried out, for example, according to the manner disclosed in the specifications of the foregoing patents. About 5 μml to about 30 μml, preferably about 8 μml to about 15 μml of an aqueous sample is spotted on the spreading layer, and incubated at a definite temperature in the range of about 20° C. to about 45° C. for a prescribed time, if necessary. Thereafter, a color change or coloring in the analytical element is measured from the side of the support by reflection photometry, and the subject component in the sample is determined by the principle of colorimetry.

EXAMPLES

Example 1

The support employed was a colorless transparent polyethylene terephthalate (PET) film having a thickness of 180 μm on which a gelatin subbing was provided. The following aqueous solution was applied on the support at the rate of 156 cc/m$^2$ and then dried to form a reagent layer having a thickness of 15 μm.

| | |
|---|---|
| Gelatin | 190 g |
| nonylphenyl polyglycidol | 8 g |

-continued

| | |
|---|---|
| (glycidol 10 units) | |
| Peroxidase | 150,000 IU |
| FAD | 240 mg |
| TPP | 1,000 mg |
| Pyruvate oxidase | 150,000 IU |
| Color Indicator* | 3.0 g |
| Water | 1,360 g |
| Adjusted to pH 6.5 by dil. NaOH solution. | |

*2-(3,5-dimethoxy-4-hydroxyphenyl)-4-phenethyl-5-(4-dimethyaminophenyl)-imidazole The following aqueous solution was applied on the reagent layer so that its dry thickness became 3 μm (60 cc/m$^2$), and then dried to form a binding layer.

| | |
|---|---|
| Gelatin | 40 g |
| Surfactant | 1.6 g |
| ("Surfactant 10 G" Olin) | |
| Water | 600 g |
| Adjusted to pH 7.0 by dil.NaOH solution. | |

The above binding layer was dampened with 30 g/m$^2$ of water. A broad woven fabric made of polyester (void volume; 9.8 μl/m$^2$) was lightly pressed on it to laminate it as the spreading layer, followed by drying.

Subsequently, the following aqueous solution was uniformly applied on the spreading layer at the rate of 100 cc/m$^2$, and dried to obtain an integral multilayer analytical element for measuring ALT activity.

| | |
|---|---|
| Trishydroxymethylaminomethane | 2.2 g |
| Potassium dihydrogenphosphate | 4.5 g |
| Sodium α-ketoglutarate | 4.0 g |
| L-Alanine | 27.5 g |
| Hydroxypropyl methyl cellulose | 8.7 g |
| ("METHOLOSE 90SH 100", SHINETSU CHEMICAL CO., LTD.) | |
| Dye | 0.7 g |
| (4,4'-Monomethine-bis-{1-(p-sulfophenyl)-3-methyl-5-pyrazolone}oxonol | |
| Polyoxyethylene octyl phenyl ether | 27 g |
| Titanium Dioxide (Rutile-type) | 70 g |
| Magnesium chloride | 2.4 g |
| Water | 880 g |
| Adjusted to pH 7.5 by dil. NaOH solution. | |

A comparative analytical element 1 was prepared in the same manner as the above example except that the dye was not added to the solution for applying on the spreading layer.

These analytical elements were placed under white fluorescent light ("NATIONAL FLUORESCENT LIGHT FLR/40S-W/M-X") at an illuminance of 800 luxes for the various duration described in Table 1.

After the irradiation, each 10 μml of a control serum containing 62 IU/1 (international units per liter) of alanine aminotransferase (ALT) was spotted on the respective analytical elements, and kept at 37° C. in a closed vessel. Their reflective optical densities at 640 nm were measured from 2.5 minutes to 4 minutes, and the rate of optical density variation per minute was determined. Then, each ALT activity was calculated by using the calibration curve prepared previously. The results are tabulated in Table 1.

TABLE 1

| Irradiation Time (Min.) | Measured Value of ALT Activity (IU/l) | |
|---|---|---|
| | Invention | Comparative |
| 0 | 62 | 62 |
| 15 | 64 | 65 |
| 30 | 65 | 76 |
| 40 | 68 | 84 |
| 60 | 74 | 92 |

As shown in Table 1, in the case of the comparative analytical element 1 not containing the oxonol dye, positive error occurred according to the increase of irradiation time. Whereas, in the case of the analytical element of the invention, the result was hardly affected by the irradiation of white fluorescent light up to 30 minutes.

Example 2

Another analytical element for measuring ALT activity was prepared in the same manner as Example 1 except that the same amount of Tartrazine was used as the dye in the solution for applying on the spreading layer instead of 4,4'-monomethine-bis-(1-(p salfophenyl) 3-methyl-5-pyrazolone)oxonol.

This analytical element and the comparative analytical element 1 prepared previously were irradiated by the same light as employed in Example 1 for the times described in Table 2.

After the irradiation, each 10 μl of a control serum containing 64 IU/l of ALT was spotted on the respective analytical element, and each ALT activity was calculated in the same manner as Example 1. The results are tabulated in Table 2.

TABLE 2

| Irradiation Time (Min.) | Measured Value of ALT Activity (IU/l) | |
|---|---|---|
| | Invention | Comparative |
| 0 | 64 | 64 |
| 15 | 66 | 68 |
| 30 | 64 | 80 |
| 60 | 65 | 92 |

As shown in Table 2, in the case of the comparative analytical element 1 not containing Tartrazine, a positive error occurred according to the increase of irradiation time. Whereas, in the case of the analytical element of the invention, the result was hardly effected by the irradiation of white fluorescent light, even for 60 minutes.

We claim:

1. In a dry-type analytical element containing an indicator having color-forming sensitivity for measuring the activity of alanine aminotransferase in a liquid sample, which has one or more water-permeable layers, at least one of the water-permeable layers being a porous spreading layer and at least one of the water-permeable layers containing alanine or its salt and α-ketoglutaric acid or its salt, the improvement comprising that at least one of the water-permeable layers contains a dye which is not the indicator and which has a maximum absorption in the range from 400 to 500 nm in an amount sufficient to prevent an increase in the color-forming sensitivity of the indicator.

2. The dry-type analytical element of claim 1 wherein said porous spreading layer is the uppermost layer of said water-permeable layers and contains alanine or its salt and α-ketoglutaric acid or its salt.

3. The dry-type analytical element of claim 1 wherein said dye is water-soluble.

4. The element of claim 1 wherein the minimum amount of dye is 30 μmole per square meter of element.

5. The element of claim 1 wherein the amount of dye is 50 μmole per square meter of element.

6. The dry-type analytical element of claim 17 wherein the dye is selected from the group consisting of cyanine dyes, merocyanine dyes, styryl dyes, oxonol dyes, hemioxonol dyes, and acidic azo dyes.

7. The dry-type analytical element of claim 1 wherein said porous spreading layer contains alanine or its salt and α-ketoglutaric acid or its salt.

8. The dry-type analytical element of claim 7 wherein a water-permeable reagent layer contains pyruvate oxidase and an indicator having a color-forming sensitivity to hydrogen peroxide.

9. The dry-type analytical element of claim 1 wherein at least one of the water-permeable layers contains pyruvate oxidase and an indicator having a color-forming sensitivity to hydrogen peroxide.

10. The dry-type analytical element of claim 9 wherein said layer containing pyruvate oxidase and said indicator is a layer other than the layer containing alanine or its salt and α-ketoglutaric acid or its salt.

11. The dry type analytical element of claim 9 wherein said layer containing pyruvate oxidase and said indicator is a layer other than the porous spreading layer.

12. The dry type and analytical element of claim 9 wherein said pyruvate oxidase is the culture product of Pediococcus, Streptococcus or Aerococcus.

13. The dry-type analytical element of claim 9 wherein said water-permeable layer contains phosphate ion source.

14. The analytical element of claim 9 wherein at said water-permeable layer contains inorganic phosphate.

15. The analytical element of claim 9 wherein said water-permeable layer containing pyruvate oxidase and the indicator is maintained at the pH of 6.5 to 8.0.

* * * * *